United States Patent [19]

Senni et al.

[11] Patent Number: 4,647,661

[45] Date of Patent: Mar. 3, 1987

[54] METHOD OF PREPARING ω-LACTAMS, IN PARTICULAR CAPROLACTAM

[75] Inventors: Paolo Senni, Colleferro; Leandro Zuliani, Buia; Sergio Ferruzzi, Trieste, all of Italy

[73] Assignee: Chimica del Friuli S.p.A., Torviscosa, Italy

[21] Appl. No.: 845,122

[22] Filed: Mar. 27, 1986

[30] Foreign Application Priority Data

Mar. 27, 1985 [IT] Italy .............................. 20089 A/85

[51] Int. Cl.$^4$ .......................................... C07D 201/10
[52] U.S. Cl. .................................. 540/537; 540/464; 546/243; 548/554
[58] Field of Search ............... 260/239.3 A; 546/243; 548/554

[56] References Cited

U.S. PATENT DOCUMENTS 3,022,291  2/1962  Muench et al. .................... 540/537
4,349,437  9/1982  Rossi et al. ......................... 540/537

Primary Examiner—Robert T. Bond
Attorney, Agent, or Firm—Wenderoth, Lind & Ponack

[57] ABSTRACT

A method of preparing ω-lactams, in particular caprolactam, comprising: a step of premixing cycloaliphatic acids having the formula

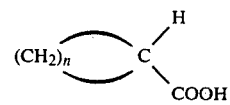

where $n = 3-13$, with a dehydrating agent; the first step of reaction with a nitrosating agent; the second step of reaction with the addition of a very small amount of water corresponding to a molar ratio $U = H_2O/SO_3$ within the 0.1 to 0.9 range; and the step of reclaiming the unreacted cycloaliphatic acid. The method affords improved output from the lactamization reaction and reduced byproducts.

17 Claims, 2 Drawing Figures

METHOD OF PREPARING ω-LACTAMS, IN PARTICULAR CAPROLACTAM

BACKGROUND OF THE INVENTION

1. Field of the Invention

This invention relates to a method of preparing ω-lactams, in particular caprolactam, with improved yield and purity.

It is known that caprolactam can be prepared by reacting cycloaliphatic compounds with a nitrosating agent in the presence of a dehydrating agent.

U.S. Pat. No. 3,356,675 and Italian Patent Application 27018 A/79 disclose preparing caprolactams from cycloaliphatic compounds, including hexahydrobenzoic acid, by reacting them with nitrosyl acid sulphate in concentrated sulphuric acid or oleum, and utilizing oleum as the dehydrating agent.

Italian Patent Application 27018 A/79 claims a process for preparing ω-lactams containing 5 to 14 carbons in a multi-stage reactor, implemented by racting a cycloaliphatic acid having the general formula

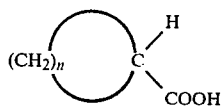

where n varies from 3 to 13, and/or the corresponding anhydrides, with a nitrosating agent in the presence of a dehydrating agent.

According to the prior art, moisture is to be removed completely from the lactamization reaction medium to avoid the need to decrease the reaction rate and selectively below an acceptable minimum. It is, in fact, known that the reaction rate and selectivity can only be increased through the use of an appropriate dehydrating agent.

Examples of cycloaliphatic acids which can be lactamized include hexahydrobenzoic acid, cyclododecanecarboxylic acid, etc. Hexahydrobenzoic acid, also referred to as cyclohexanecarboxylic acid, being preferred.

As the nitrosating agent, any of the agents specified in U.S. Pat. No. 3,356,675 may be used.

Nitrosyl sulphuric acid is preferred for the production of caprolactam. Known dehydrating agents are: $SO_3$, chlorosulphonic acid, anhydride of chlorosulphonic acid, phosphoric anhydride, or even the very anhydride of hexahydrobenzoic acid, in which case, in calculating the molar ratios, one mole anhydride of hexahydrobenzoic acid is the equivalent of one mole $SO_3$; thus, for simplicity, reference will be made hereinafter to $SO_3$-equivalent moles, to specify either one mole $SO_3$ or one mole of some other anhydride serving the same anhydrifying function.

The reaction temperature can vary in the range of 30° to 100° C., and in particular where hexahydrobenzoic acid is used, the reaction temperature would be preferably in the 60° to 90° C. range.

The reaction may be conducted in either discontinuous, semicontinuous, or continuous stirred reactors.

A continuous multi-stage reactor would be preferred with hexahydrobenzoic acid, anyhow.

Thermal regulation of the reaction (which is markedly exothermic) may be effected by using, in the reaction system, a particular inert thermostating solvent which can remove reaction heat by absorption as evaporation heat, thereby constancy of the reaction temperature is achieved by boiling the thermostating solvent.

Examples of thermostating solvents are: cyclohexane, n-eptane, n-hexane, n-pentane, chlorinated or fluorinated hydrocarbons, nitrocompounds, etc.

It is known to conduct the lactamization reaction in conformity with the following sequence of process steps:

1. Premixing step: wherein mixing is carried out at a low temperature, i.e. in the range of 0° to 40° C., of the hexahydrobenzoic acid with the dehydrating agent (e.g. oleum at a concentration in the 30% to 37% range); during this step, there occurs formation of a mixed anhydride which, in the instance of caprolactam, comprises cyclohexanecarboxysulphonic anhydride.

2. First reaction step: wherein there occurs the lactamization reaction between the mixed anhydride and the nitrosating agent (e.g. nitrosylsulphuric acid in oleum). This step takes place according to the continuous method within a multistage reactor where the nitrosating agent is fed into each of the stages at a temperature in the 30° C. to 100° C. range. This method affords excellent control of the reaction exothermicity through the above-mentioned thermostating solvent.

3. Second reaction step: wherein the reaction is completed and no nitrosating agent is fed; this step takes place in a multistage system, in series and/or within an external reactor (post-reactor) at a temperature in the 30° C. to 100° C. range.

4. Unreacted hexahydrobenzoic acid reclaiming step: wherein low temperature hydrolysis (approximately 20° C.+30° C.) is carried out of the reaction mass along with the extraction of the hexahydrobenzoic acid by the same thermostating solvent.

The control parameters of this reaction are:

Molar ratios of load and temperature $SO_3S_{tot}$-NOAEB(*).

(*)hexahydrobenzoic acid.

By operating in accordance with these prior methods, on an industrial scale, the following lactamization outputs are to be obtained, when expressed as kmoles of caprolactam yielded per kmole hexahydrobenzoic acid ($\eta AEB$).

$$\eta_{AEB} = 0.85 + 0.90$$

Furthermore, the byproducts that forms when operating in accordance with prior methods are of four types:

i. strongly acidic byproducts to be obtained by sulphonation, in the reaction conditions, of the alpha-carbon in the carboxylic group of hexahydrobenzoic acid; cyclohexane-carboxylic acid is formed which represents the largest percent amount of all the byproducts formed;

ii. byproducts with a weak acid function (carboxylic acids), such as ε-amino-capronic-N-hexahydrobenzoyl, ε-amino-valeric-N-hexahydrobenzoyl, etc.;

iii. neutral byproducts, such as lactones, amides, nitriles, etc.;

iv. high polarity byproducts which are, therefore, readily soluble in water; this byproduct family also represents an important reasons for not achieving higher outputs.

SUMMARY OF THE INVENTION

Accordingly, it is an object of this invention to arrange for an improved caprolactam output.

A further object of this invention is to arrange for decreased production of the strongly acidic byproducts (i) which form the outstanding proportion of all the byproducts formed.

These and other objects are achieved by a method according to the invention, which comprises the following steps:

a. a premixing step wherein cycloaliphatic acids having the general formula

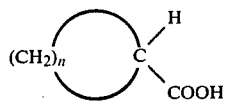

where n=3-13 and/or their corresponding anhydrides are mixed with a dehydrating agent;

b. a first reaction step wherein a nitrosating agent and the mixture from step 1 are introduced into a reactor maintained at a temperature in the 30° to 100° C. range;

c. a second reaction step wherein the lactamization reaction is completed at a temperature range of 30° to 100° C.;

d. a step of reclaim of the unreacted cycloaliphatic acid; the improvement consisting of that, during said second reaction step, water is added in a very small amount corresponding to a molar ratio $U = H_2O/SO_3$ equivalents in the 0.1 to 0.90 range.

The molar ratio of dehydrating agent to nitrosating agent is preferably with the range of 0.7 to 1.1. The small amount of water which is added during the second reaction step is such that a by-weight concentration of $SO_3$ equivalents is obtained which ranges from 2% to 10% of the reaction mass. That amount is preferably within the range of 5% to 6% where hexahydrobenzoic acid is used as the cycloaliphatic acid.

The dehydrating agent is preferably oleum at a concentration in the 36% to 50% range, preferably in the 38% to 40% range where hexahydrobenzoic acid is used as the cycloaliphatic acid. These concentration levels are significantly higher than the oleum concentration employed with prior methods (30% to 37%).

Furthermore, where hexahydrobenzoic acid is used as cycloaliphatic acid, the molar ratio U would be preferably in the 0.4 to 0.6 range; the temperature of the first and second reaction steps is preferably in the 60° to 80° C. range. The small amount water which is added during the second reaction step may be in the form of an acqueous solution containing sulphuric acid and possibly ω-lactams.

The method of this invention is preferably conducted on a continuous basis through a plurality of consecutive stages which implement said first and second reaction steps. Preferably, said plural consecutive stages would be split in two serially arranged discrete reactors. The first of the reactors receives the nitrosating agent and completes the markedly exothermic part of the lactamization reaction. No nitrosating agent is preferably added through the last stages of the first reactor.

The second of the reactors receives the small amount water and completes the low-exothermic part of the reaction.

The unreacted cycloaliphatic acid reclaiming step is carried out by hydrolysis with water of the product from the second reactor, that hydrolysis process being conducted at a temperature preferably in the 20° to 30° C. range. The hydrolyzed product is separated into an acqueous phase containing ω-lactams and an organic phase containing the unreacted cycloaliphatic acid and the thermostating solvent.

DETAILED DESCRIPTION OF THE PREFERRED EMBODIMENT

The invention may be more clearly understood by making reference to the following non-limitative examples and the accompanying illustrative drawings, where:

Figure 1:
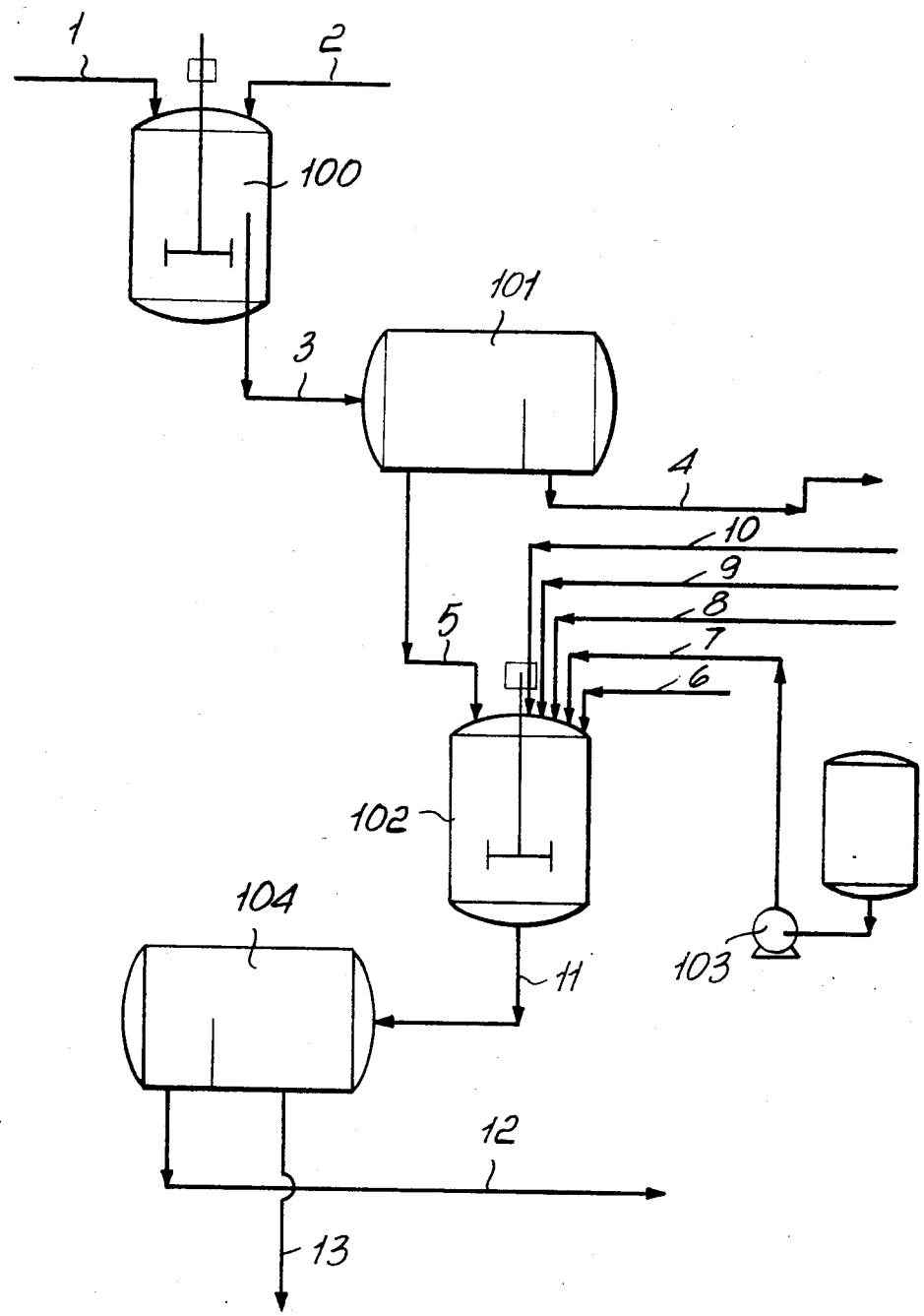
FIG. 1 is a block diagram of a semi-continuous method.

Examples 1-6 relate to FIG. 1. Examples 1, 3 and 5 illustrate the method of this invention, and Examples 2, 4 and 6 are comparative examples of the prior art.

Figure 2:
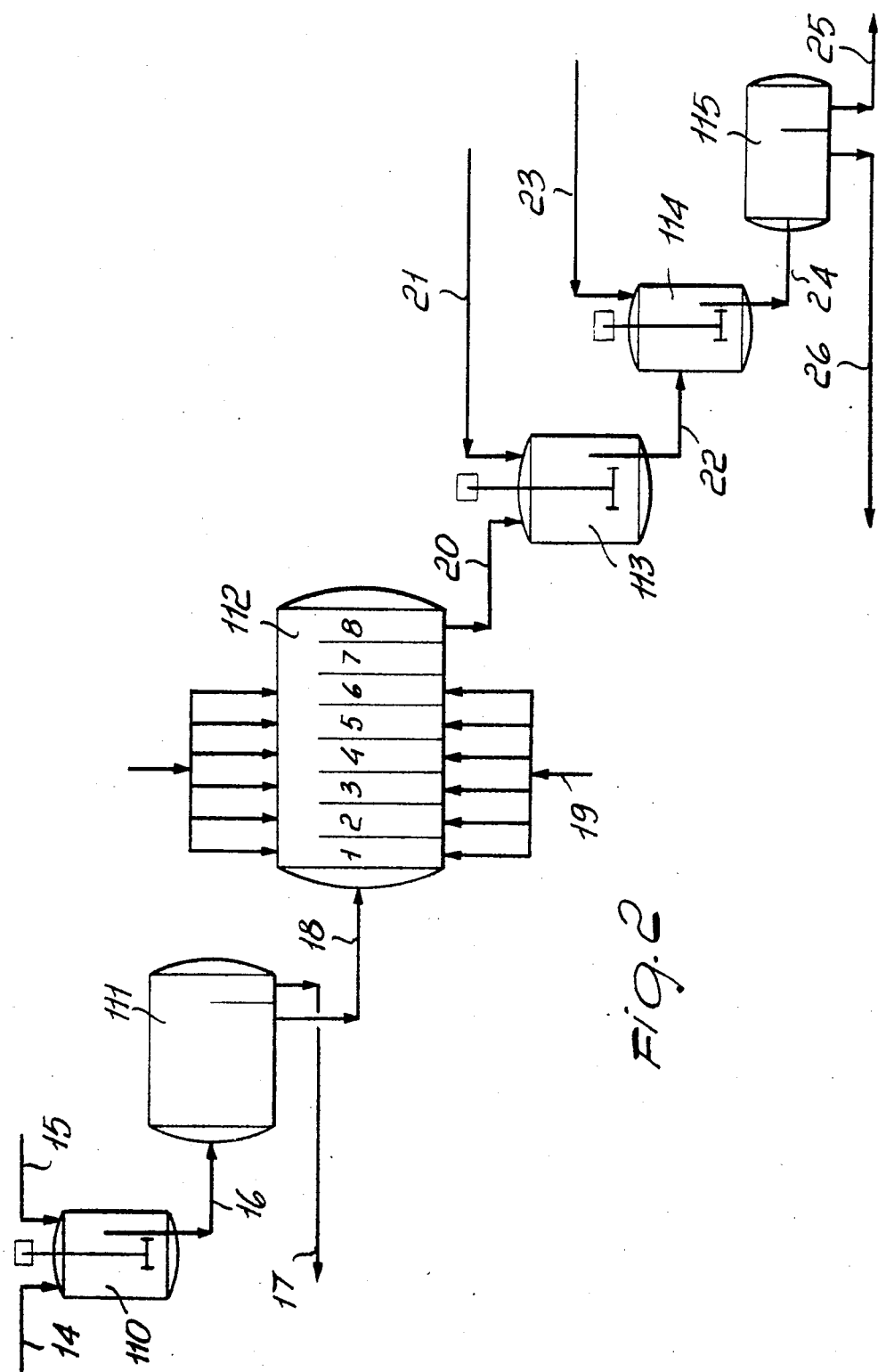
FIG. 2 is a block diagram of a continuous method.

Examples 7 and 8 relate to FIG. 2. Example 7 shows the method of this invention, and Example 8 is a comparative example of the prior art.

Throughout the charts:

AEB = hexahydrobenzoic acid
SP = byproducts
CL = caprolactam
ACCSH = cyclohexanecarbonysulphuric acid

EXAMPLES 1-6

Examples 1-6 have been conducted as semi-continuous tests (with only the nitrosylsulphuric acid solution being fed continuously) on the system shown in FIG. 1.

The method steps are:

(a) formation of the premix; this operation has been carried out in a glass-lined reactor 100 having a volume of 700 ml, wherethrough cooled water was circulated to maintain a premixing temperature of 20° C. Loade first were the hexahydrobenzoic acid solution, byproducts of the hexahydrobenzoic acid, and the n-hexane solvent 1, and then let dripping slowly under powerful agitation so as to keep the temperature at 20° C., and the oleum 2 was added in the desired concentration. All this was then transferred as at 3 into a separator (settling) funnel 101 and the n-hexanic phase 4 was separated from the sulphuric phase 5.

(b) First lactamization step: this operation was carried out in a glass reactor 102 with a 2,000 ml capacity equipped with an internal heat exchanger adapted for connection to a source of hot water (at 90° C.) and/or a source of cold water (at 15° C.) and with a mechanical turbine stirrer. The sulphuric phase 5 was loaded into the reactor and an amount of solvent (n-hexane) 6 was added. Stirring was commenced and by circulating hot water (90° C.) through the heat exchanger, the pre-mix temperature was raised from 20° C. to 71°-72° C., setting the time lapse for bringing the pre-mix temperature from 35° C. to 71°-72° C. (=heating time). Thereafter, the reactor has been fed with the solution of nitrosylsulphuric acid 7 from a metering pump 103, in oleum (=nitrose), within 12 minutes.

(c) Second lactamization reaction: on completion of the step of adding nitrose, the reaction mass was held at the test temperature for 3 minutes (beginning of the maturing time), and then the water 8 was added into the reactor to quench some of the $SO_3$, and the whole held under agitation at a constant temperature for 10 minutes (=maturing time). Lastly, the mass was cooled by circulating cold water (at about 15° C.) through the heat exchanger, setting the time for lowering the temperature from 71°-72° C. down to 30° C. (=mass cooling time).

(d) Unreacted hexahydrobenzoic acid reclaiming step: on the temperature of the reaction mass dropping down to about 20° C., the hydrolysis water 9 was begun to be added while holding the temperature low (at about 20° C.), thereby separating the unreacted hexahydrobenzoic acid from the solution of caprolactam in diluted sulphuric acid. The biphase mix 11 was then discharged quantitatively into a separator funnel 104 flushing the reactor with n-hexane 10, thereby to obtain an n-hexane phase 12 containing hexahydrobenzoic acid and a sulphuric phase 13 which contained caprolactam, lactamization byproducts, and to a lesser amount, hexahydrobenzoic acid.

EXAMPLES 7 AND 8

Examples 7 and 8 have been conducted as continuous tests on an industrial system depicted in FIG. 2.

The method several steps were as follows:

(a) Formation of the pre-mix: this operation has been carried out in a lined reactor 110, wherethrough cooled water was circulated to hold the pre-mixing temperature at 20° C. The solution of hexahydrobenzoic acid, byproducts of the hexahydrobenzoic acid, and the n-hexane solvent 1 has been loaded, and then dripped slowly and under powerful agitation, so as to hold the temperature at 20° C., the oleum 15 is added at the concentration sought. Then, the whole 16 is transferred into a separator (settling) funnel 111, and the n-hexane phase 17 is separated from the sulphuric phase 18.

(b) First lactamization step: this operation is carried out in a reactor 112. The reactor comprises 7 separator partitions arranged in cascade, thereby the reaction mix, in falling from one partition down onto the next, forms a plurality of consecutive reaction stages. The sulphuric phase 18 was loaded into the reactor 112, and an amount of solvent (n-hexane) added. The solution of nitrosulphuric acid in oleum (=nitrose) 19 was then added within 12 minutes.

(c) Second lactamization step: on completion of the nitrose adding operation, the reaction mass in the last two stages 7 and 8 of the reactor 112 has been held at the test temperature for 3 minutes (beginning of the maturing time), and thereafter, the reaction mix was transferred with the line 20 of the reactor 113 there was added into the reactor 113 the water 23 to quench some of the $SO_3$, and the whole was held under agitation at a constant temperature for 10 minutes.

(d) Unreacted hexahydrobenzoic acid reclaiming step: the reaction products from step (c) were transferred over the line 22 to the hydrolyzer 114, whereinto there is added the hydrolysis water 23, while holding the temperature low (at about 20° C.), to produce separation of the unreacted hexahydrobenzoic acid from the caprolactam solution in diluted sulphuric acid. The biphase mix 24 was then discharged quantitatively into a decanter 115, flushing the reactor with n-hexane, so as to obtain an n-hexane phase 25 which contains hexahydrobenzoic acid and byproducts and a sulphuric phase 26 containing caprolactam, lactamization byproducts, and to a lesser amount, hexahydrobenzoic acid.

It may be seen from the tables that the invention affords a considerable reduction in the byproducts (i) and (ii) which form together nearly all of the byproducts yield.

In particular, this invention allows the $SO_3$ concentration to be increased during the first reaction step; this results in decreased byproducts (iv), and decreased concentration of $SO_3$ in the second reaction step, which affords decreased byproducts (i). As may be taken from the Tables, to that decrease in byproducts there corresponds an increased caprolactam yield.

| | AEB (g) | SP (g) | n-hexane (g) | $SO_3$ (g) | $H_2SO_4$ (g) | $NOHSO_4$ (g) | $H_2O$ (g) | CL (g) | ACCSH (g) | Total (g) |
|---|---|---|---|---|---|---|---|---|---|---|
| | | | | | EXAMPLE No. 1 | | | | | |
| 1 | 282.2 | 24.5 | 91.7 | | | | | | | 398.4 |
| 2 | | | | 70.2 | 107.5 | | | | | 177.7 |
| 3 | 282.2 | 24.5 | 91.7 | 70.2 | 107.5 | | | | | 576.1 |
| 4 | 5.7 | 15.9 | 72.3 | | | | | | | 93.9 |
| 5 | 276.5 | 8.6 | 19.4 | 70.2 | 107.5 | | | | | 482.3 |
| 6 | | | 133.0 | | | | | | | 133.0 |
| 7 | | | | 6.7 | 44.0 | 127.0 | | | | 177.7 |
| 8 | | | | | | | 9.5 | | | 9.5 |
| 9 | | | | | | | 154.5 | | | 154.5 |
| 10 | | | 200.0 | | | | | | | 200.0 |
| 11 | 153.7 | 11.5 | 352.4 | | 340.6 | | 147.3 | 103.1 | 6.4 | 1115.0 |
| 12 | 141.5 | 3.4 | 352.4 | | | | | | | 497.3 |
| 13 | 12.2 | 8.1 | | | 340.6 | | 147.3 | 103.1 | 6.4 | 617.7 |

LOAD MOLAR RATIOS  
$SO_3/NO =$ 0.96  
$S_{tot}/NO =$ 3.51  
$AEB/NO =$ 2.16  
$H_2O/SO_3 =$ 0.55  
REACTION YIELDS  
$\eta AEB =$ 95.1

| | AEB (g) | SP (g) | n-hexane (g) | $SO_3$ (g) | $H_2SO_4$ (g) | $NOHSO_4$ (g) | $H_2O$ (g) | CL (g) | ACCSH (g) | Total (g) |
|---|---|---|---|---|---|---|---|---|---|---|
| | | | | | EXAMPLE No. 2 | | | | | |
| 1 | 282.2 | 24.5 | 91.7 | | | | | | | 398.4 |
| 2 | | | | 70.2 | 107.5 | | | | | 177.7 |
| 3 | 282.2 | 24.5 | 91.7 | 70.2 | 107.5 | | | | | 576.1 |
| 4 | 5.7 | 15.9 | 72.3 | | | | | | | 93.9 |
| 5 | 276.5 | 8.6 | 19.4 | 70.2 | 107.5 | | | | | 482.3 |
| 6 | | | 133.0 | | | | | | | 133.0 |
| 7 | | | | 6.7 | 44.0 | 127.0 | | | | 177.7 |
| 8 | | | | | | | | | | — |

-continued

| | EXAMPLE No. 2 | | | | | | | | |
|---|---|---|---|---|---|---|---|---|---|
| | AEB (g) | SP (g) | n-hexane (g) | $SO_3$ (g) | $H_2SO_4$ (g) | $NOHSO_4$ (g) | $H_2O$ (g) | CL (g) | ACCSH (g) | Total (g) |
| 9 | | | | | | 164.0 | | | | 164.0 |
| 10 | | | 200.0 | | | | | | | 200.0 |
| 11 | 148.2 | 12.0 | 352.4 | | 336.7 | | 148.0 | 103.1 | 14.8 | 1115.2 |
| 12 | 136.2 | 3.4 | 352.4 | | | | | | | 492.0 |
| 13 | 12.0 | 8.6 | | | 336.7 | | 148.0 | 103.1 | 14.8 | 623.2 |

LOAD MOLAR RATIOS
$SO_3/NO$ = 0.96
$S_{tot}/NO$ = 3.51
$AEB/NO$ = 2.16
$H_2O/SO_3$ = no water in the post-reactor REACTION YIELDS   $\eta AEB$ = 91.0

| | EXAMPLE No. 3 | | | | | | | | |
|---|---|---|---|---|---|---|---|---|---|
| | AEB (g) | SP (g) | n-hexane (g) | $SO_3$ (g) | $H_2SO_4$ (g) | $NOHSO_4$ (g) | $H_2O$ (g) | CL (g) | ACCSH (g) | Total (g) |
| 1 | 286.9 | 21.5 | 95.7 | | | | | | | 404.1 |
| 2 | | | | 70.1 | 78.3 | | | | | 148.4 |
| 3 | 286.9 | 21.5 | 95.7 | 70.1 | 78.3 | | | | | 552.5 |
| 4 | 5.3 | 15.8 | 77.5 | | | | | | | 98.6 |
| 5 | 281.6 | 5.7 | 18.2 | 70.1 | 78.3 | | | | | 453.9 |
| 6 | | | 133.0 | | | | | | | 133.0 |
| 7 | | | | 7.5 | 42.2 | 127.0 | | | | 176.7 |
| 8 | | | | | | | 10.3 | | | 10.3 |
| 9 | | | | | | | 143.0 | | | 143.0 |
| 10 | | | 200.0 | | | | | | | 200.0 |
| 11 | 158.6 | 9.2 | 351.2 | | 310.5 | | 136.4 | 103.2 | 6.6 | 1075.7 |
| 12 | 146.7 | 2.7 | 351.2 | | | | | | | 500.6 |
| 13 | 11.9 | 6.5 | | | 310.5 | | 136.4 | 103.2 | 6.6 | 575.1 |

LOAD MOLAR RATIOS
$SO_3/NO$ = 0.97
$S_{tot}/NO$ = 3.20
$AEB/NO$ = 2.20
$H_2O/SO_3$ = 0.59

REACTION YIELDS   $\eta AEB$ = 95.0

| | EXAMPLE No. 4 | | | | | | | | |
|---|---|---|---|---|---|---|---|---|---|
| | AEB (g) | SP (g) | n-hexane (g) | $SO_3$ (g) | $H_2SO_4$ (g) | $NOHSO_4$ (g) | $H_2O$ (g) | CL (g) | ACCSH (g) | Total (g) |
| 1 | 286.9 | 21.5 | 95.7 | | | | | | | 404.1 |
| 2 | | | | 70.1 | 78.3 | | | | | 148.4 |
| 3 | 286.9 | 21.5 | 95.7 | 70.1 | 78.3 | | | | | 552.5 |
| 4 | 5.3 | 15.8 | 77.5 | | | | | | | 98.6 |
| 5 | 281.6 | 5.7 | 18.2 | 70.1 | 78.3 | | | | | 453.9 |
| 6 | | | 133.0 | | | | | | | 133.0 |
| 7 | | | | 7.5 | 42.2 | 127.0 | | | | 176.7 |
| 8 | | | | | | | | | | — |
| 9 | | | | | | | 153.3 | | | 153.3 |
| 10 | | | 200.0 | | | | | | | 200.0 |
| 11 | 153.2 | 9.2 | 351.2 | | 306.2 | | 135.8 | 103.0 | 15.8 | 1074.4 |
| 12 | 141.9 | 2.7 | 351.2 | | | | | | | 495.8 |
| 13 | 11.3 | 6.5 | | | 306.2 | | 135.8 | 103.0 | 15.8 | 578.6 |

LOAD MOLAR RATIOS
$SO_3/NO$ = 0.97
$S_{tot}/NO$ = 3.20
$AEB/NO$ = 2.20
$H_2O/SO_3$ = no water in the post-reactor REACTION YIELDS   $\eta AEB$ = 90.8

| | EXAMPLE No. 5 | | | | | | | | |
|---|---|---|---|---|---|---|---|---|---|
| | AEB (g) | SP (g) | n-hexane (g) | $SO_3$ (g) | $H_2SO_4$ (g) | $NOHSO_4$ (g) | $H_2O$ (g) | CL (g) | ACCSH (g) | Total (g) |
| 1 | 287.4 | 21.6 | 98.7 | | | | | | | 407.7 |
| 2 | | | | 59.7 | 102.8 | | | | | 162.5 |
| 3 | 287.4 | 21.6 | 98.7 | 59.7 | 102.8 | | | | | 570.2 |
| 4 | 5.8 | 16.7 | 72.6 | | | | | | | 95.1 |
| 5 | 281.6 | 4.9 | 26.1 | 59.7 | 102.8 | | | | | 475.1 |
| 6 | | | 133.0 | | | | | | | 133.0 |
| 7 | | | | 7.5 | 42.2 | 127.0 | | | | 176.7 |
| 8 | | | | | | | 7.6 | | | 7.6 |

EXAMPLE No. 5

| | AEB (g) | SP (g) | n-hexane (g) | SO$_3$ (g) | H$_2$SO$_4$ (g) | NOHSO$_4$ (g) | H$_2$O (g) | CL (g) | ACCSH (g) | Total (g) |
|---|---|---|---|---|---|---|---|---|---|---|
| 9 | | | | | | | 146.6 | | | 146.6 |
| 10 | | 200.0 | | | | | | | | 200.0 |
| 11 | 156.5 | 16.3 | 359.1 | | 322.6 | | 139.6 | 97.2 | 5.8 | 1097.1 |
| 12 | 144.7 | 2.9 | 359.1 | | | | | | | 506.7 |
| 13 | 11.8 | 13.4 | | | 322.6 | | 139.6 | 97.2 | 5.8 | 590.4 |

LOAD MOLAR RATIOS
- SO$_3$/NO = 0.84
- S$_{tot}$/NO = 3.32
- AEB/NO = 2.20
- H$_2$O/SO$_3$ = 0.50

REACTION YIELDS
- $\eta$AEB = 0.88

EXAMPLE No. 6

| | AEB (g) | SP (g) | n-hexane (g) | SO$_3$ (g) | H$_2$SO$_4$ (g) | NOHSO$_4$ (g) | H$_2$O (g) | CL (g) | ACCSH (g) | Total (g) |
|---|---|---|---|---|---|---|---|---|---|---|
| 1 | 287.4 | 21.6 | 98.7 | | | | | | | 407.7 |
| 2 | | | | 59.7 | 102.8 | | | | | 162.5 |
| 3 | 287.4 | 21.6 | 98.7 | 59.7 | 102.8 | | | | | 570.2 |
| 4 | 5.8 | 16.7 | 72.6 | | | | | | | 95.1 |
| 5 | 281.6 | 4.9 | 26.1 | 59.7 | 102.8 | | | | | 475.1 |
| 6 | | | 133.0 | | | | | | | 133.0 |
| 7 | | | | 7.5 | 42.2 | 127.0 | | | | 176.7 |
| 8 | | | | | | | | | | |
| 9 | | | | | | | 154.2 | | | 154.2 |
| 10 | | 200.0 | | | | | | | | 200.0 |
| 11 | 155.1 | 16.3 | 359.1 | | 321.4 | | 139.8 | 97.2 | 8.3 | 1097.2 |
| 12 | 143.1 | 3.0 | 359.1 | | | | | | | 505.2 |
| 13 | 12.0 | 13.3 | | | 321.4 | | 139.8 | 97.2 | 8.3 | 592.0 |

LOAD MOLAR RATIOS
- SO$_3$/NO = 0.84
- S$_{tot}$/NO = 3.32
- AEB/NO = 2.20
- H$_2$O/SO$_3$ = no water in the post-reactor REACTION YIELDS
- $\eta$AEB = 0.87

EXAMPLE No. 7

| | AEB (Kg/h) | SP (Kg/h) | n-hexane (Kg/h) | SO$_3$ (Kg/h) | H$_2$SO$_4$ (Kg/h) | NOHSO$_4$ (Kg/h) | H$_2$O (Kg/h) | CL (Kg/h) | ACCSH (Kg/h) | Total (Kg/h) |
|---|---|---|---|---|---|---|---|---|---|---|
| 14 | 6980 | 790 | 2201 | | | | | | | 9971 |
| 15 | | | | 1484 | 2348 | | | | | 3832 |
| 16 | 6980 | 790 | 2201 | 1484 | 2348 | | | | | 13803 |
| 17 | 341 | 620 | 1042 | | | | | | | 2003 |
| 18 | 6639 | 170 | 1159 | 1484 | 2348 | | | | | 11800 |
| 19 | | | | 220 | 863 | 2706 | | | | 3789 |
| 20 | 4021 | 203 | 4029 | 1639 | 5300 | | | 2196 | 160 | 17548 |
| 21 | | | | | | | 221 | | | 221 |
| 22 | 4021 | 203 | 4029 | 656 | 6504 | | | 2196 | 160 | 17769 |
| 23 | | | | | | | 3279 | | | 3279 |
| 24 | 4021 | 203 | 4029 | | 7307 | | 3132 | 2169 | 160 | 21048 |
| 25 | 3831 | 62 | 4029 | | | | | | | 7922 |
| 26 | 190 | 141 | | | 7307 | | 3132 | 2196 | 160 | 13126 |

LOAD MOLAR RATIOS
- SO$_3$/NO = 1.00
- S$_{tot}$/NO = 3.54
- AEB/NO = 2.43
- H$_2$O/SO$_3$ = 0.58

REACTION YIELDS
- $\eta$AEB = 95.0%

EXAMPLE No. 8

| | AEB (Kg/h) | SP (Kg/h) | n-hexane (Kg/h) | SO$_3$ (Kg/h) | H$_2$SO$_4$ (Kg/h) | NOHSO$_4$ (Kg/h) | H$_2$O (Kg/h) | CL (Kg/h) | ACCSH (Kg/h) | Total (Kg/h) |
|---|---|---|---|---|---|---|---|---|---|---|
| 14 | 6980 | 790 | 2201 | | | | | | | 9971 |
| 15 | | | | 1484 | 2348 | | | | | 3832 |
| 16 | 6980 | 790 | 2201 | 1484 | 2348 | | | | | 13803 |
| 17 | 341 | 620 | 1042 | | | | | | | 2003 |
| 18 | 6639 | 170 | 1159 | 1484 | 2348 | | | | | 11800 |
| 19 | | | | 220 | 863 | 2706 | | | | 3789 |
| 20 | 4021 | 203 | 4029 | 1639 | 5300 | | | 2196 | 160 | 17548 |
| 21 | | | | | | | | | | — |
| 22 | 3906 | 244 | 4029 | 1593 | 5300 | | | 2196 | 280 | 17548 |

-continued

EXAMPLE No. 8

| | AEB (Kg/h) | SP (Kg/h) | n-hexane (Kg/h) | SO$_3$ (Kg/h) | H$_2$SO$_4$ (Kg/h) | NOHSO$_4$ (Kg/h) | H$_2$O (Kg/h) | CL (Kg/h) | ACCSH (Kg/h) | Total (Kg/h) |
|---|---|---|---|---|---|---|---|---|---|---|
| 23 | | | | | | | 3466 | | | 3466 |
| 24 | 3906 | 244 | 4029 | | 7251 | | 3108 | 2196 | 280 | 21014 |
| 25 | 3716 | 63 | 4029 | | | | | | | 7808 |
| 26 | 190 | 181 | | | 7251 | | 3108 | 2196 | 280 | 13206 |
| LOAD MOLAR RATIOS | | | | | SO$_3$/NO = | | 1.00 | | | |
| | | | | | S$_{tot}$/NO = | | 3.54 | | | |
| | | | | | AEB/NO = | | 2.43 | | | |
| | | | | | H$_2$O/SO$_3$ | | no water in the post-reactor | | | |
| REACTION YIELDS | | | | | $\eta$AEB = | | 91% | | | |

We claim:

1. A method of preparing ω-lactams containing 5 to 14 carbon atoms, comprising the following steps:
   (a) a pre-mixing step wherein cycloaliphatic acids having the general formula

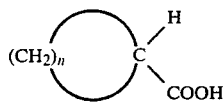

where n=3-13 and/or the corresponding anhydrides are mixed with a dehydrating agent;
   (b) a first reaction step wherein a nitrosating agent and the mixture of step 1 are introduced into a reactor maintained at a temperature in the 30° to 100° C. range;
   (c) a second reaction step wherein the lactamization reaction is brought to completion at a temperature in the 30° to 100° C. range;
   (d) an unreacted cycloaliphatic acid reclaiming step; the improvement consisting of that
   during said second reaction step, water is added in small amount corresponding to a molar ratio U=H$_2$O/SO$_3$ equivalents in the 0.1 to 0.90 range.

2. A method according to claim 1, wherein said ratio U is in the range of 0.4 to 0.6.

3. A method according to claim 1, wherein the molar ration of the dehydrating agent to the nitrosating agent lies between 0.7 and 1.1.

4. A method according to claim 1, wherein said cycloaliphatic acid is hexahydrobenzoic acid and said temperature of the first and second reaction steps is in the 60° to 80° C. range.

5. A method according to claim 1, wherein the dehydrating agent is oleum employed at a concentration in the 36% to 50% range.

6. A method according to claim 5, wherein the concentration of said oleum is in the 38% to 40% range.

7. A method according to claim 1, wherein the small amount water added during the second reaction step is such as to contain a concentration of SO$_3$ equivalents by weight lying between 2% and 10% of the reaction mass.

8. A method according to claim 7, wherein said by-weight concentration of SO$_3$ equivalents lies between 5% and 6% of the reaction mass.

9. A method according to claim 1, wherein said small amount water is added in acqueous solution form.

10. A method according to claim 9, characterized in that said acqueous solution comprises sulphuric acid.

11. A method according to claim 9, characterized in that said acqueous solution comprises ω-lactams.

12. A method according to claim 1, wherein said steps (b) and (c) of the reaction are conducted continuously through a plurality of consecutive stages.

13. A method according to claim 12, characterized in that said plurality of consecutive stages is split in two serially arranged discrete reactors, into a first of said two reactors there being introduced said nitrosating agent, and into the second of said two reactors there being introduced small amount water.

14. A method according to claim 1, wherein said unreacted cycloaliphatic acid reclaiming step (d) comprises hydrolysis of the reaction product, followed by separation of an acqueous phase containing ω-lactams and an organic phase containing cycloaliphatic acid non-reacted.

15. A method according to claim 14, wherein said hydrolysis is conducted at a temperature in the 20° to 30° C. range.

16. A method according to claim 1, wherein said dehydration agent is selected from chlorosulphonic acid, phosphoric anhydride, or anhydride of hexahydrobenzoic acid.

17. A method according to claim 1, wherein said cycloaliphatic acid is selected from hexahydrobenzoic acid, cyclododecane carboxylic acid, and the anhydrides of said cycloalkancarboxylic acids.

* * * * *